United States Patent [19]

Wood

[11] Patent Number: 5,373,651
[45] Date of Patent: Dec. 20, 1994

[54] SMART SHOES

[76] Inventor: Thomas L. Wood, 33 Maple Dr., Colts Neck, N.J. 07722

[21] Appl. No.: 57,044

[22] Filed: May 3, 1993

[51] Int. Cl.⁵ .......................... A43B 5/00; A61B 5/103
[52] U.S. Cl. ........................................ 36/114; 36/1; 36/136
[58] Field of Search ...................... 36/1, 114, 132, 136

[56] References Cited

U.S. PATENT DOCUMENTS

| | | | |
|---|---|---|---|
| 4,466,204 | 8/1984 | Wu | 36/136 |
| 4,510,704 | 4/1985 | Johnson | 36/136 |
| 4,771,394 | 9/1988 | Cavanagh | 36/132 |
| 4,814,661 | 3/1989 | Ratzlaff et al. | 36/136 |
| 5,042,504 | 8/1991 | Huberti | 128/779 |
| 5,065,321 | 11/1991 | Bezos et al. | 364/424.04 |
| 5,209,240 | 5/1993 | Jain et al. | 128/779 |

*Primary Examiner*—Paul T. Sewell
*Assistant Examiner*—Marie Denise Patterson

[57] ABSTRACT

This invention permits a wearer of this footwear to measure the number and the force of steps that have been taken by the user during a predetermined interval. The wearer can subsequently transfer the step information into a computer for further analysis. In a particular embodiment, the information transfer is accomplished using an inductively coupled data link between the footwear and the computer.

2 Claims, 8 Drawing Sheets

| VALID SMART SHOE COMMAND CODE WORDS |
|---|
| ATTN (160) |
| INQ (161) |
| RESET (162) |
| RESPOK (163) |

| VALID SMART SHOE RESPONSE CODE WORDS |
|---|
| READY (164) |
| RESPQ (165) |
| RESETOK (166) |
| OK (167) |

Figure 3

SMART SHOES

TECHNICAL FIELD

This invention relates to the electronic monitoring of human physical activity, and in particular to athletic footwear that facilitates such.

BACKGROUND OF THE INVENTION

Typically, several methods are used to measure the amount of energy expended by an individual during an aerobic workout. The most usual is for the person exercising to keep a steady pace of work for a set amount of time. This results in an indirect measurement of the energy used by the person exercising. Charting the length and intensity of the workout is manual and error-prone. Alternatively, one can use an instrumented machine to directly measure the amount of work that has been done. This type of workout is limited by the configuration of the instrumented machine. These specialized machines are equipped with an on-board microprocessor to monitor a user's activities.

This invention adds an apparatus to the footwear used by the individual to permit a direct measurement of the work performed during an exercise session while permitting a wide variety of styles of exercise to be instrumented. The invention also facilitates the accurate recording of an exercise session by a data transmission facility incorporated into the design. The data transmission is accomplished using a method which permits the data transfer between computer and instrumented footwear to proceed without interfering with other, possible concurrent data transfer sessions.

Athletic footwear has already appeared on the market that has some amount of active electronics built in, an example of this is the athletic shoes that have light emitting diodes ("LED's") that flash when the user walks. This invention adds a processor unit such as a microcontroller or a microprocessor, to each shoe to capture the user's activity and a data transfer coupling to transfer this activity log to a computer (such as a personal computer ("PC")) later use.

BRIEF DESCRIPTION OF THE DRAWINGS

FIG. 3 is a table providing a list of the basic command/response set supported by the athletic shoe of FIG. 1A;

DETAILED DESCRIPTION OF THE INVENTION

Figure 1A:
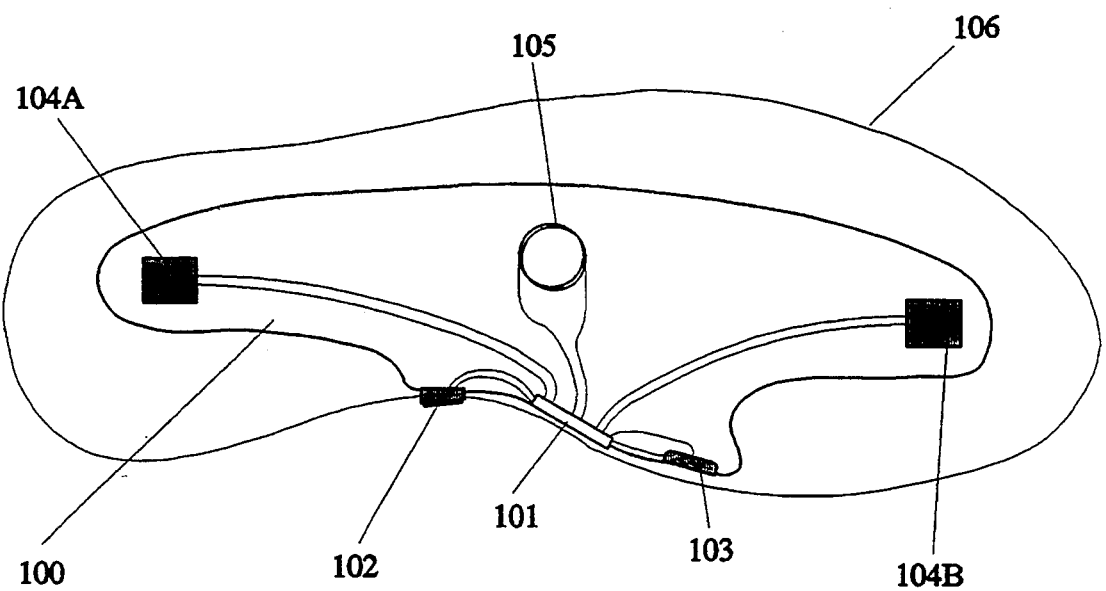
FIG. 1A is a bottom view of an athletic shoe incorporating a particular embodiment of the invention.
Figure 1B:
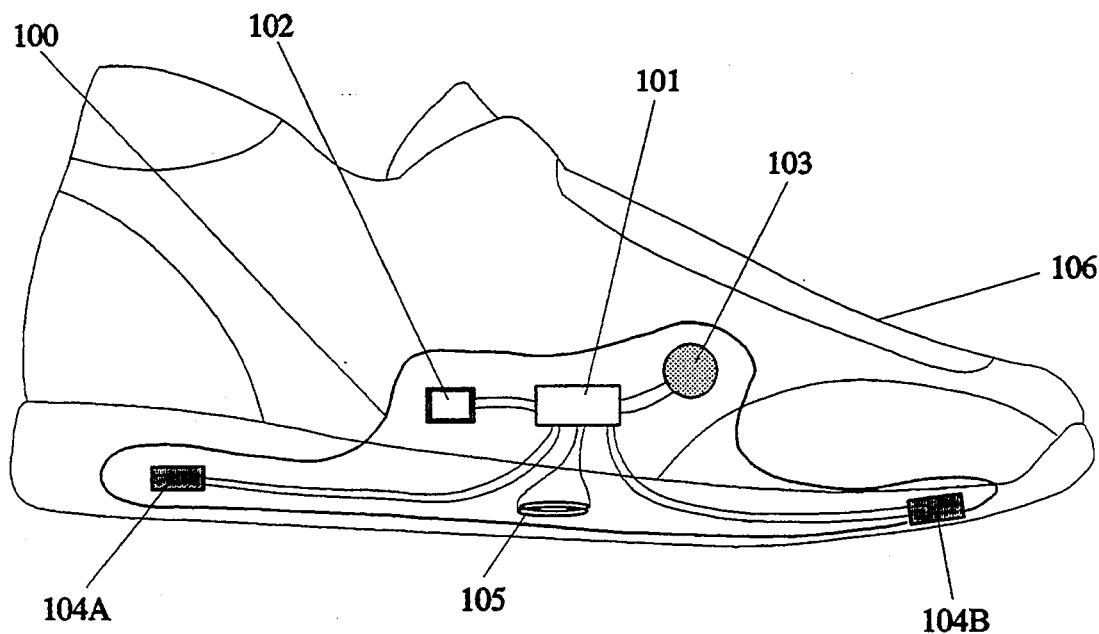
FIG. 1B is a side view of the athletic shoe shown in FIG. 1A.

FIGS. 1A and 1B show a particular embodiment of the invention. The invention adds an apparatus 100 to the footwear 106 that consists of a microcontroller 101, a set of pressure sensors 104A and 104B, a data transfer coupling 105, a user reset button 102, and a battery 103.

The microcontroller senses the output of the pressure sensor to determine how many and how much force is being exerted on the shoe by the wearer. This information is stored in the microcontrollers on-board memory until it is reset by the user, this data is referred to as the workout data. The user can accomplish this by manually resetting the counter using the reset button on each shoe, or by causing a reset command to be sensed by the microcontrollers inductive interface.

Figure 1C:
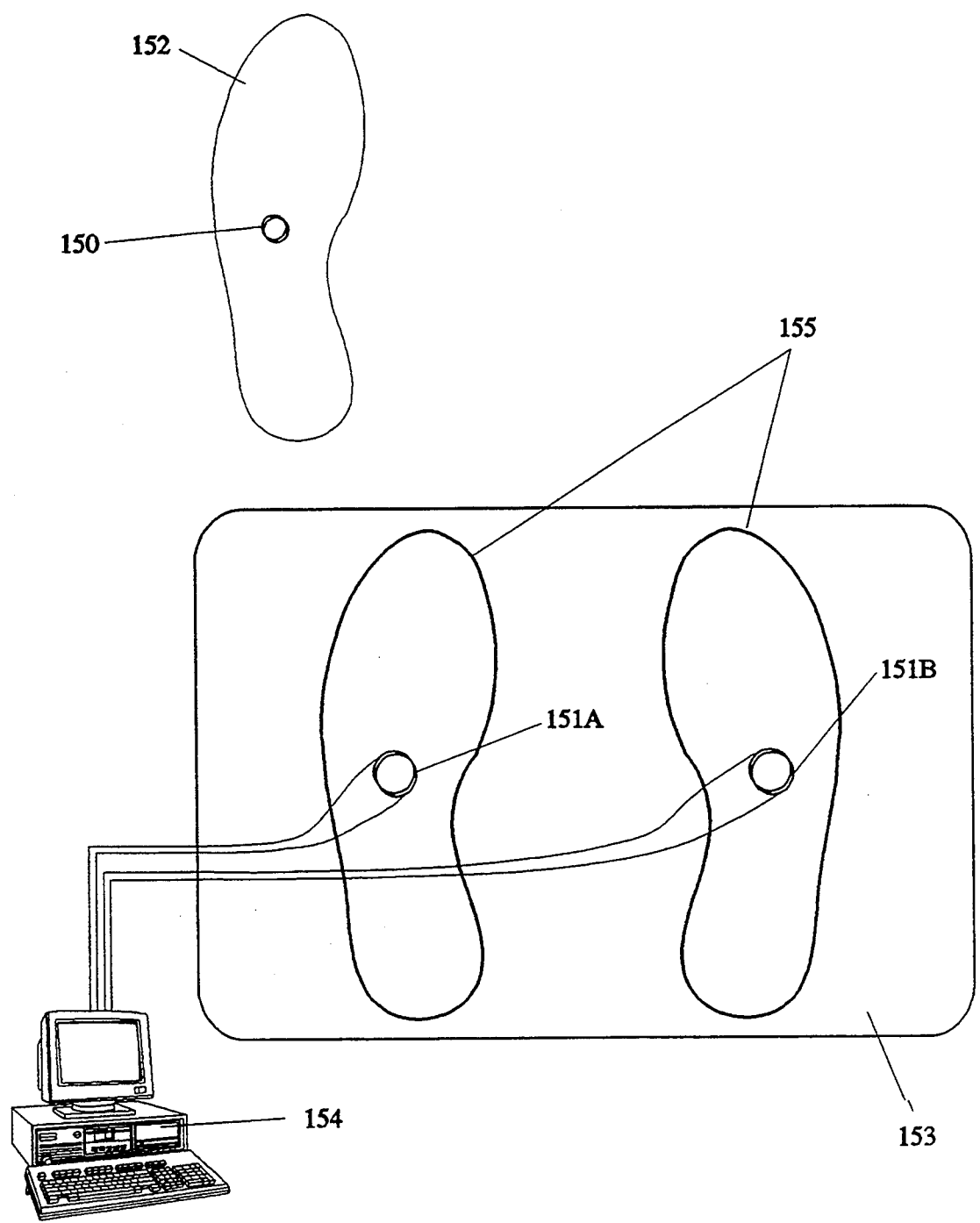
FIG. 1C is top view of a transfer mat adapted to accept data from the athletic shoe of FIG. 1A.

FIG. 1C depicts a simplified diagram of the interface between a PC and the Smart Shoe ("SS"). An inductive interface 150, also referred to as the data transfer coupling, built into the SS 152, is used to transfer the workout data to an attached computer 154 for possible long term storage and analysis. To effect the interface between each shoe and the computer, the shoe 152 is placed on a designated spot on the data transfer mat 153 as shown in FIG. 1C. The spot is chosen to place the shoe's inductive loop 150 in close physical proximity to the corresponding inductive loop in the data transfer mat 151. Normally the wearer of the SS simply stands on the data mat with each shoe over an outline 155 of a shoe that is on the data transfer mat. This eliminates interference from other instrumented shoes that may be in use in the local vicinity. The use of an inductive interface, rather than requiring direct contact between the electronics of the shoe and the electronics of the data gathering computer, permits the electronics of the shoe to be completely enclosed from the elements, avoiding problems due to corrosion of the electronics and data transfer problems due to bad connections.

The inductive interface is accomplished by using a number of concentric windings 151 built into the sole of the athletic shoe 152. These windings 151 are excited by similar windings 151 that are located in a specially designed mat 153. The mat's windings are electrically connected to the PC 154, which will receive and store the data. The pair of windings or coils 150,151 are used to both send and receive signals.

Products have been on the market for some time, which permit a hearing aid to be inductively coupled to a telephone receiver. This coupling permits the voice band information to be received by the user of the hearing aid without requiring a wired electrical connection between the hearing aid and the telephone receiver. This inductive coupling is capable of passing voice grade frequency information from the telephone receiver circuit to the hearing aid. The same amount of bandwidth is all that is required to transmit data using a pair of dial-up modems. An embodiment of this invention could use, but need not be limited to a frequency shift keying data modulation technique to pass digital information between the data source and sink. This technique is widely used today in low speed modems. This invention uses these two concepts together to implement a data transfer mechanism between the athletic footwear and a computer. In addition, a data transfer protocol is used to synchronize the microcontroller and the PC, facilitate efficient data transfer, and ensure data integrity.

Information is sent by an attached computer to the data transfer mat, and then the attached computer awaits a reply. The dialogue between the attached computer and the microcontroller built into the athletic shoe follows a specific set of sequences 140, 141 (called a protocol) which is detailed in FIG. 2.

Figure 2:
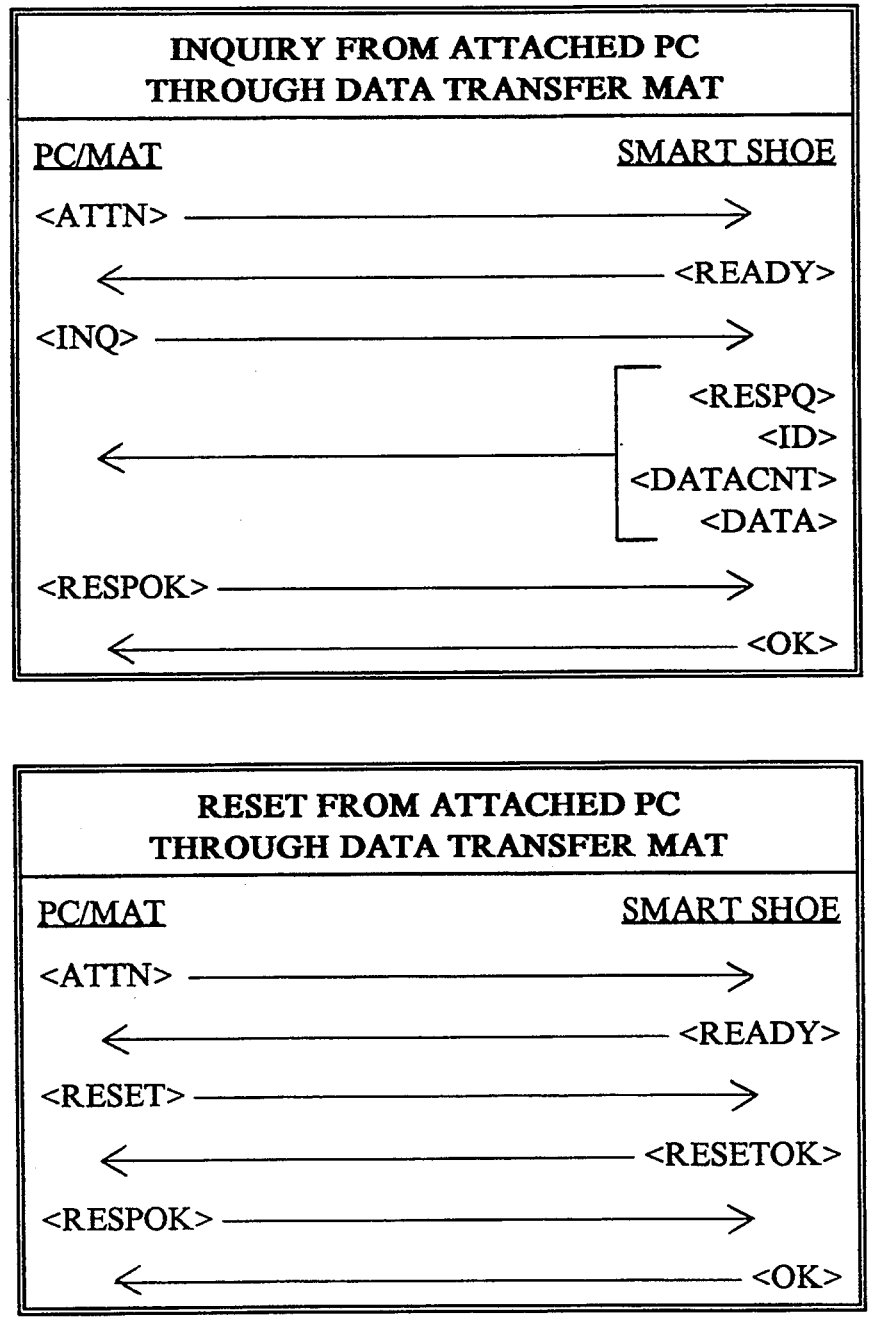
FIG. 2 is a table providing a depiction of the dialogue between the personal computer 154 of FIG. 1C and the microcontroller 101 of FIG. 1A.

When the shoe based microcontroller detects an inquiry from its inductive interface, it then replies using the protocol sequence 140 depicted in FIG. 2. This results in the transfer of any resident workout data to the attached computer. Additionally, the protocol sequence 141 in FIG. 2, can be used to communicate a RESET command from the attached PC to the SS. This action results in a reset of all of the workout data that is currently resident on the microcontrollers data memory. It is anticipated that other command/response dialogues could be added to the protocol at a future data to extend the functionality of the interface. The table shown in FIG. 3 lists the basic command/response set supported by the Smart Shoe. The ATTN command 160 is used to signify the SS that a command will be issued by the PC. Valid response is READY 164. The INQ command 161 is used by the PC to request the contents of the SS data memory. Valid response is RESQ 165, followed by the SS identification number, and then the contents of SS data memory. The RESET command 162 is used to reset the SS data memory to the initialized state. Valid response is RESETOK 166. The RESPOK command 163, is used by the PC to indicate the SS reply has been accepted by the PC. Valid response is OK 167.

Figure 4A:
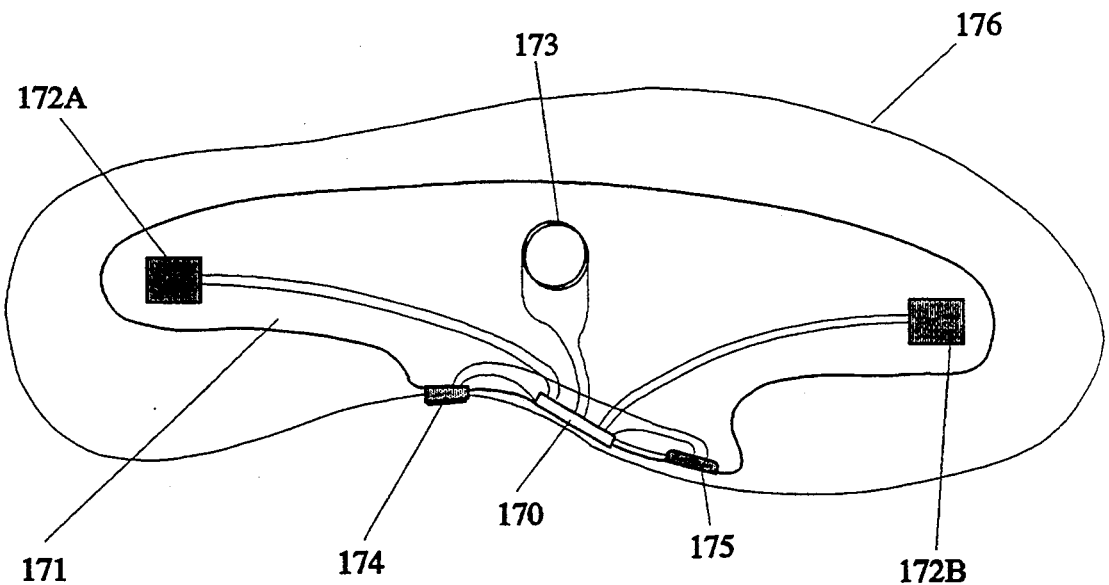
FIG. 4A is a bottom view of an athletic shoe incorporating a particular embodiment of the invention.
Figure 4B:
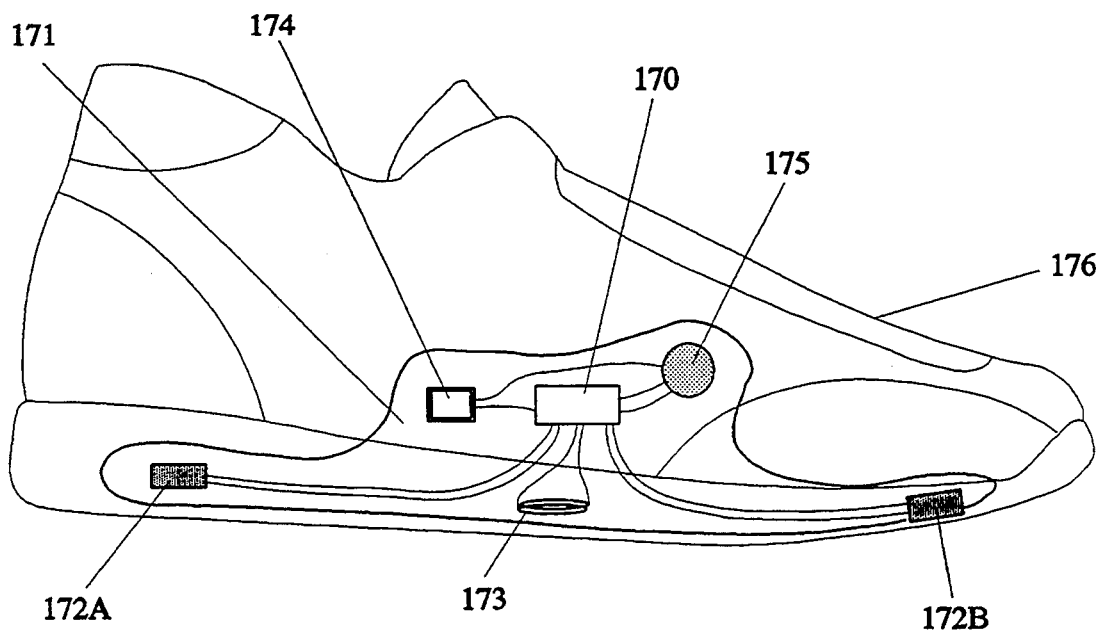
FIG. 4B is a side view of the athletic shoe shown in FIG. 1A.

FIGS. 4A and 4B depict another embodiment of this invention incorporated into an athletic shoe 176. The microcontroller 170 is built on a flexible printed circuit membrane 171 that is attached to the inside portion of the shoe's upper. The flexible circuit membrane 171 is run down the side of the shoe and in between the layers of the shoe's sole connecting the microcontroller to the pressure sensors 172A and 172B, and the inductive loop 173. A reset button 174 is also connected to the microcontroller 170.

The on-board microcontroller has three tasks that it executes: 1) it monitors the reset button to determine if the user has reset that button; 2) it monitors the inductive interface for commands; and 3) it monitors the output of the pressure sensors. Flow diagrams are depicted in FIGS. 5A, 5B and 5C for the three tasks described above.

DESCRIPTION OF THE FLOW DIAGRAM FIGURES

Monitor Reset Button

Figure 5A:
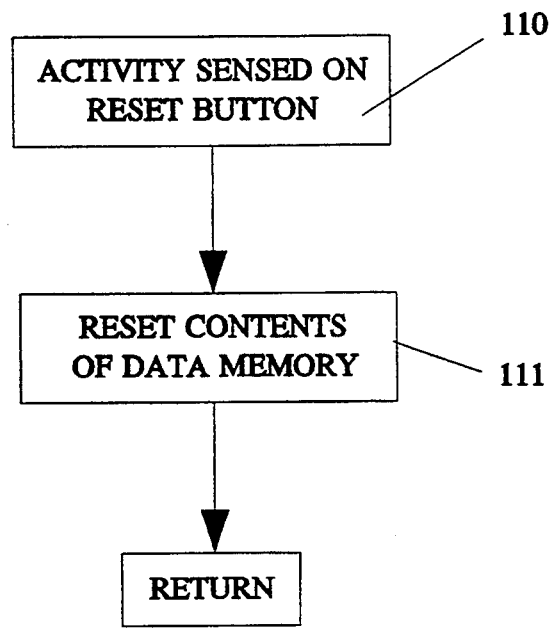
FIG. 5A is a flow diagram depicting the operations executed upon depressing the monitor reset button on the athletic shoe of FIG. 4A.
Figure 5B:
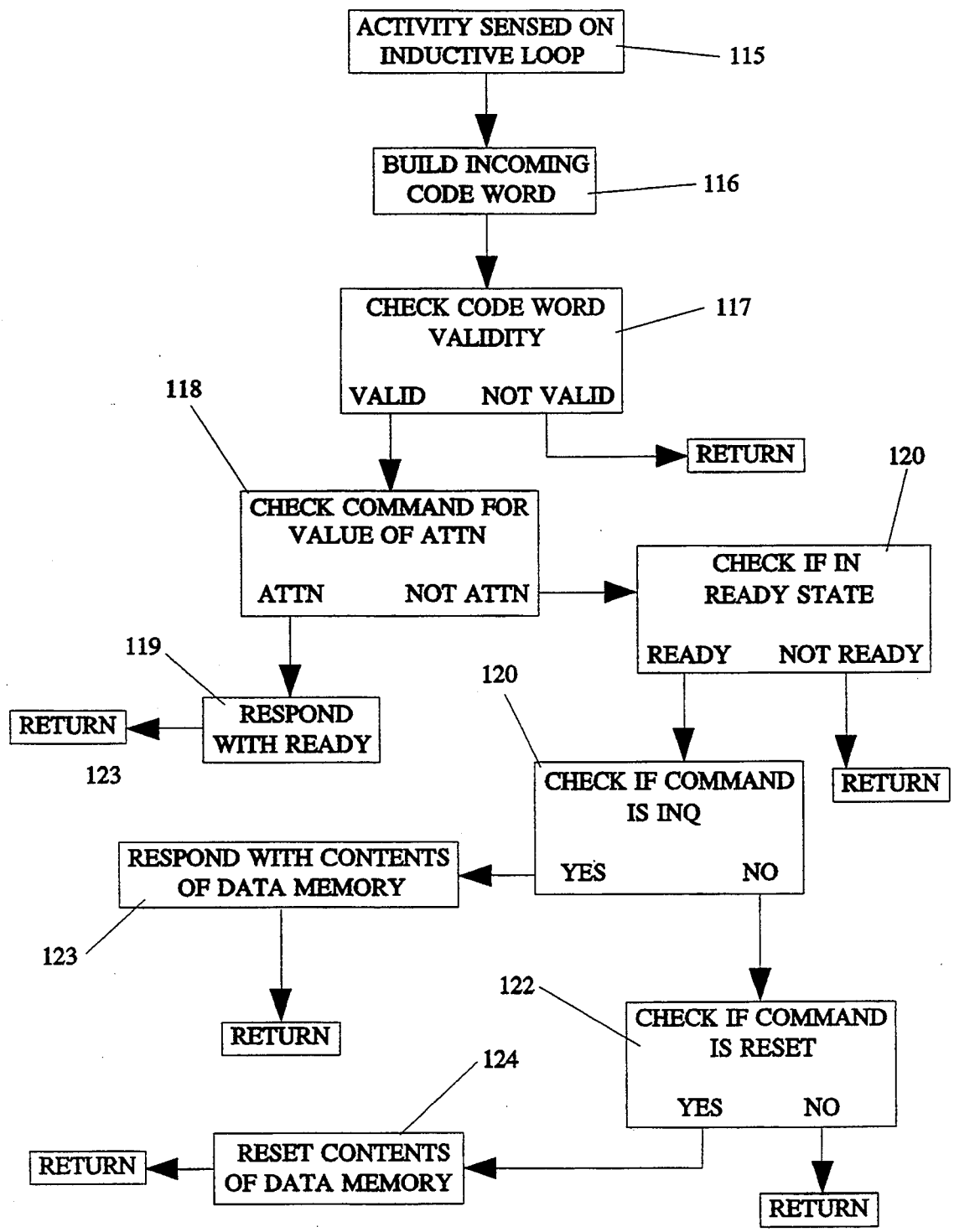
FIG. 5B is a flow diagram depicting the operations executed when data is transferred via the inductive loop located within the athletic shoe of FIG. 4A.
Figure 5C:
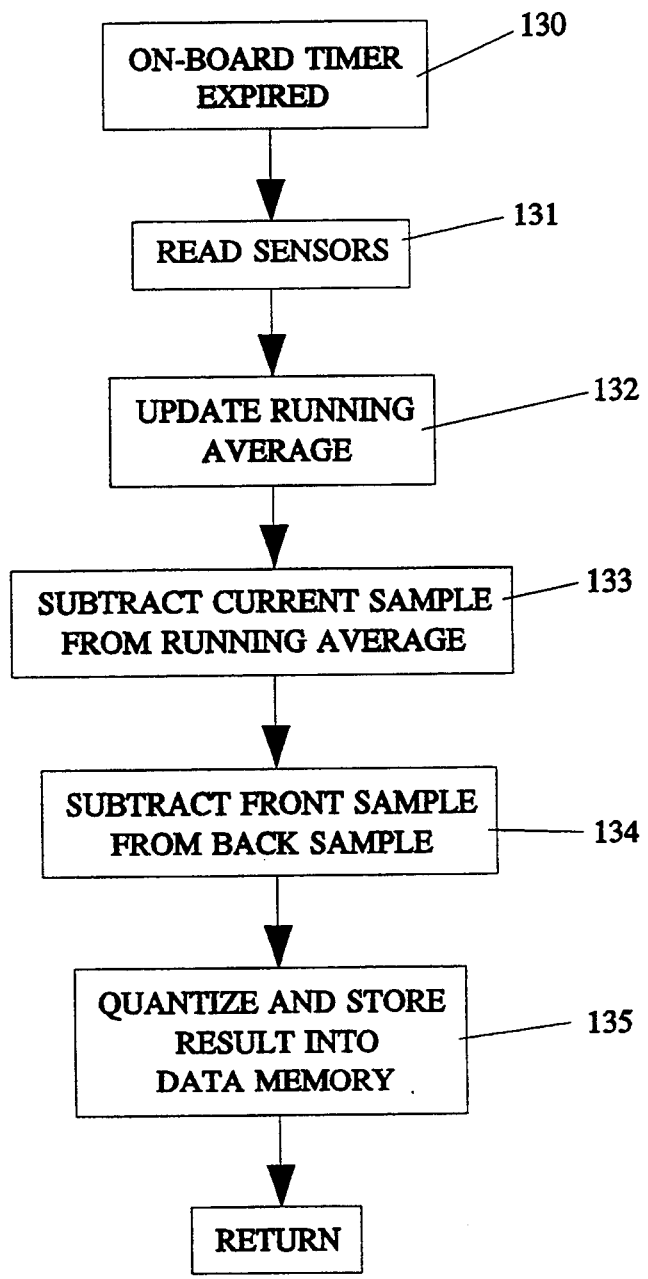
FIG. 5C is a flow diagram depicting the operations executed during the monitoring of pressure via the pressure sensors located within the athletic shoe of FIG. 4A.

Please refer to FIGS. 4A, 4B and 5A with respect to the following discussion. The user depresses the reset button 174 on the side of the athletic shoe. One contact of this button is connected to the microcontroller 170, and other contact is connected to the power source 175. A change in voltage is detected upon the contact connected to the microcontroller 170 when the button is depressed, and consequently, microcontroller resets the workout data 111.

Monitor Inductive Loop

Please refer to FIGS. 4A, 4B and 5B with respect to the following discussion. Inductive loop 173 is connected to microcontroller 170. Activity is sensed by the microcontroller 115 by comparing the levels of these lines. Incoming data are constructed by the microcontroller by recording the patterns of activity on the I/O pins 116. This builds the incoming command words. The incoming data is then validated 117 and compared against the pre-stored command words 118, 121, 122 that are listed in the table shown in FIG. 3. The microcontroller either accepts the commands 119, 123, 122, and performs the appropriate action 123, 124, or returns to an idle state without taking any action. This latter case can occur if the proper protocol sequence was not followed by the PC.

Monitor Pressure Sensors

Please refer to FIGS. 4A, 4B and 5C with respect to the following discussion. Each of the pressure sensors 136 are monitored for changes. One is located in the heel area, and the other is located in the toe area. Each sensor is connected to the microcontroller 170. Every ½ sec 130, each sensor is polled 131, producing a pressure sample. The workout data is extracted from the pressure sample by pre-compensating each pressure sensor output using a running average 132 of the last one hundred and twenty (120) samples over a 1 minute period 133. This value is then used to calculate the difference 134 between the front and rear sensors. This result is then quantized to one of 20 levels (thresholds) and a corresponding count is then incremented 135. This set of counts constitutes the workout data.

It will be understood that the particular embodiments described above are only illustrative of the principles of the present invention, and that various modifications could be made by those skilled in the art without departing from the scope and spirit of the present invention, which is limited only by the claims that follow. One such modification might include a grid of pressure sensors in both the heel and toe sections of the shoe, permitting detailed data to be collected and stored, which could later be transferred to the PC (using the data transfer mat) and analyzed. This invention might be used as a part of a physical therapy program, either in sports medicine, accident recovery or a pediatric program.

What is claimed:

1. A system for collecting data from an athletic shoe comprising:
   an activity log computer;
   a mat including at least one inductive interface linked to said activity log computer;
   an athletic shoe including a plurality of pressure sensors, a microprocessor, a memory and an inductive coupling, said microprocessor being adapted to receive from said plurality of pressure sensors data related to the force exerted upon said athletic shoe, store said received data in said memory, and transmit said stored data to said activity computer via said inductive interface and said inductive coupling, and said microprocessor being further adapted to receive and respond to information from said activity computer via said inductive interface and said inductive coupling.

2. The invention of claim 1 further comprising a reset means upon the exterior of said athletic shoe adapted to clear any data stored within said memory.

* * * * *